United States Patent
Baxi et al.

(10) Patent No.: US 9,044,172 B2
(45) Date of Patent: Jun. 2, 2015

(54) ERGONOMIC DETECTION, PROCESSING AND ALERTING FOR COMPUTING DEVICES

(75) Inventors: Amit S. Baxi, Thane (West) (IN); Vivek N. Darera, Bangalore (IN); Vincent S. Mageshkumar, Koparkhairane Navi Mumbai (IN)

(73) Assignee: Intel Corporation, Santa Clara, CA (US)

( * ) Notice: Subject to any disclaimer, the term of this patent is extended or adjusted under 35 U.S.C. 154(b) by 803 days.

(21) Appl. No.: 12/884,481

(22) Filed: Sep. 17, 2010

(65) Prior Publication Data

US 2011/0080290 A1    Apr. 7, 2011

(51) Int. Cl.
*A61B 5/00*    (2006.01)
*A61B 5/11*    (2006.01)

(52) U.S. Cl.
CPC ............. *A61B 5/1116* (2013.01); *A61B 5/4528* (2013.01); *A61B 2503/24* (2013.01); *A61B 5/6823* (2013.01)

(58) Field of Classification Search
CPC .. A61B 5/1116; A61B 5/6823; A61B 5/4528; G06F 19/3418; G01P 15/18
USPC ................ 340/573.7, 573.1, 540, 500, 407.1, 340/407.2; 600/920, 300, 301, 595
See application file for complete search history.

(56) References Cited

U.S. PATENT DOCUMENTS

| | | | | |
|---|---|---|---|---|
| 5,917,405 A * | 6/1999 | Joao | ........................ | 340/426.17 |
| 6,400,285 B1 * | 6/2002 | Gifford | ........................... | 341/22 |
| 6,669,286 B2 * | 12/2003 | Iusim | ........................ | 297/217.4 |
| 7,109,872 B2 * | 9/2006 | Balaban et al. | ............ | 340/573.7 |
| 7,233,312 B2 * | 6/2007 | Stern et al. | ..................... | 345/156 |
| 7,315,249 B2 * | 1/2008 | Littell | ........................ | 340/573.7 |
| 7,394,385 B2 * | 7/2008 | Franco et al. | .............. | 340/573.1 |
| 8,024,202 B2 * | 9/2011 | Carroll et al. | ..................... | 705/3 |
| 8,083,693 B1 * | 12/2011 | McKeon et al. | .............. | 600/594 |
| 8,217,797 B2 * | 7/2012 | Ikoyan | ........................ | 340/573.7 |
| 2001/0015792 A1 * | 8/2001 | Fateh et al. | ..................... | 351/239 |
| 2004/0010328 A1 * | 1/2004 | Carson et al. | ..................... | 700/90 |
| 2007/0055185 A1 * | 3/2007 | Trandafir et al. | .............. | 601/90 |
| 2009/0324024 A1 * | 12/2009 | Worthington | .................. | 382/118 |
| 2010/0198374 A1 * | 8/2010 | Carson et al. | ................... | 700/90 |
| 2011/0032098 A1 * | 2/2011 | Yang | ............................ | 340/540 |
| 2011/0275939 A1 * | 11/2011 | Walsh et al. | .................. | 600/473 |

* cited by examiner

*Primary Examiner* — Van Trieu
*Assistant Examiner* — Royit Yu
(74) *Attorney, Agent, or Firm* — Blakely, Sokoloff, Taylor & Zafman LLP (57) ABSTRACT

Methods, apparatuses and systems receive information, via at least one sensor, indicating an ergonomic characteristic of a user of a computing device. The information is user to determine if the ergonomic characteristic of the user is within a reference ergonomic boundary. In response to determining the ergonomic characteristic of the user is not within the reference ergonomic boundary, processing is executed to determine an adjustment for the user to make so that the ergonomic characteristic of the user is within the reference ergonomic boundary, the adjustment to include at least one of an adjustment to the ergonomic characteristic of the user and an adjustment to the computing device.

18 Claims, 5 Drawing Sheets

ERGONOMIC DETECTION, PROCESSING AND ALERTING FOR COMPUTING DEVICES

FIELD

Embodiments of the invention generally pertain to ergonomics related to the use of computing devices and specifically to processing information from at least one sensor to determine the ergonomic characteristics of a user of a computing device, provide feedback to the user if the user's ergonomics are incorrect, and to store data related to the ergonomic characteristics for further analysis.

BACKGROUND

Computer users find it difficult to establish and maintain proper ergonomics during computer use. Often times, a user does not know his interactions with a computer are ergonomically improper until he incurs an injury, e.g., Repetitive Strain Injury (RSI). For businesses whose employees use computers, RSI injuries may lead to a significant number of work days lost.

Even if a user is made aware of sound ergonomic practices, he often slips back into poor ergonomic practices while engrossed in work. The current state of the art solutions to notify a user of poor ergonomics are extremely limited. Some solutions simply monitor the time a user is working on a computer, and signal a reminder to "take a break" from working. Other solutions simply monitor a single element of ergonomics, e.g., a person's back posture, with no regard to what activity that person is engaged in.

BRIEF DESCRIPTION OF THE DRAWINGS

The following description includes discussion of figures having illustrations given by way of example of implementations of embodiments of the invention. The drawings should be understood by way of example, and not by way of limitation. As used herein, references to one or more "embodiments" are to be understood as describing a particular feature, structure, or characteristic included in at least one implementation of the invention. Thus, phrases such as "in one embodiment" or "in an alternate embodiment" appearing herein describe various embodiments and implementations of the invention, and do not necessarily all refer to the same embodiment. However, they are also not necessarily mutually exclusive.

Descriptions of certain details and implementations follow, including a description of the figures, which may depict some or all of the embodiments described below, as well as discussing other potential embodiments or implementations of the inventive concepts presented herein. An overview of embodiments of the invention is provided below, followed by a more detailed description with reference to the drawings.

DETAILED DESCRIPTION

Embodiments of the present invention relate to methods, apparatuses and systems to intelligently monitor ergonomic characteristics of a computing device user and determine ergonomic adjustments for the user to make. Embodiments of the present invention may be represented by a sensor or a plurality of sensors coupled to either the user or the computing device.

A sensor or a plurality of sensors may capture ergonomic data of a user of a computing device. In the embodiments discussed below, the sensors discussed by example are generally hardware devices (e.g., infrared sensor, image sensor, microphone); however, those skilled in the art know that a "sensor" may be any device or module capable of measuring a physical quantity and converting that measurement into data or tracking aspects of computing device usage.

The captured ergonomic data may include data related to user's ergonomic position with respect to the computing device (e.g., posture, distance between user and computer), the user's interaction with the computing device (e.g., interaction with a keyboard of the computing device, interaction with a display of the computing device), and the placement of components of the computing device (e.g., keyboard and display placement relative to the user). This data may be further processed to determine whether the user's ergonomics characteristics are within a reference ergonomic boundary (e.g., a stored value of "good" ergonomic characteristics). Ergonomic characteristics of a computing device user, as discussed below, are to be understood as any physical interaction between the user and components of the computing device.

After the sensor data is processed, the present invention may immediately alert the user that an ergonomic adjustment should be made. The user may be alerted by any audio, visual or tactile feedback via the sensor (if coupled to the user), the display of the computing device, or some combination thereof.

Figure 1:
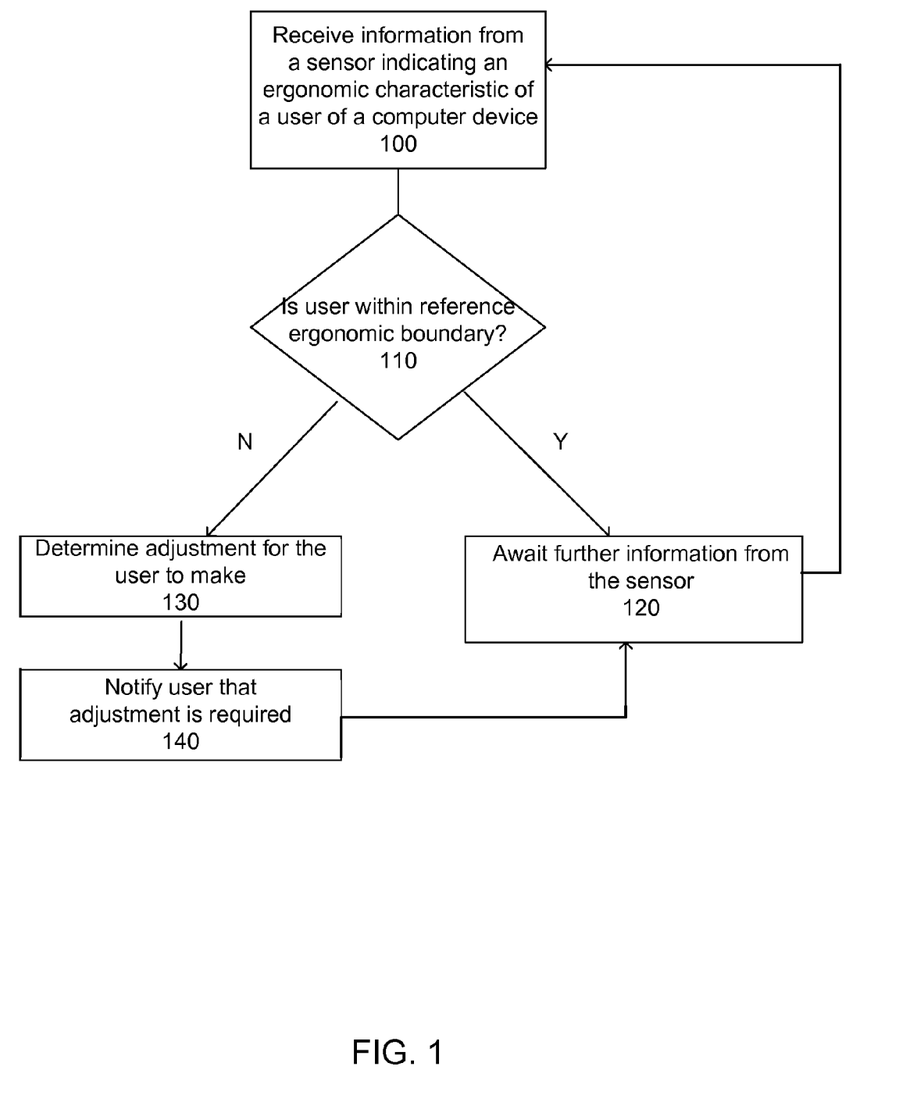
FIG. 1 is a flow diagram of an embodiment of a process for ergonomic data capture and processing.

FIG. 1 is a flow diagram of an embodiment of a process for ergonomic data capture and processing. Flow diagrams as illustrated herein provide examples of sequences of various process actions. Although shown in a particular sequence or order, unless otherwise specified, the order of the actions can be modified. Thus, the illustrated implementations should be understood only as examples, and the illustrated processes can be performed in a different order, and some actions may be performed in parallel. Additionally, one or more actions can be omitted in various embodiments of the invention; thus, not all actions are required in every implementation. Other process flows are possible.

Information is received, from at least one sensor, indicating an ergonomic characteristic of a user of a computing device, 100. The sensor may either be coupled to the user or the computing device. In one embodiment, the sensor is coupled to the user in order to determine the ergonomic posture of the user. In another embodiment, the sensor is coupled to the computing device to determine the placement and the position of parts of the computing device (e.g., position of the computer display, position of the keyboard). The computing device may be, for example, a desktop computing solution, a laptop or a netbook. Those skilled in the art know that each of the above example computing devices requires different ergonomic interactions by its users.

Information captured by the sensor may comprise orientation information (e.g., via an orientation sensor, such as an accelerometer, gyroscope, opto-mechanical sensor, rolling ball sensor, magnetic sensor, mercury sensor), audio/visual information relating to the user's interaction with the computing device (e.g., via a microphone/camera), and positional data related to the user's ergonomic position with respect to the computing device (e.g., via a membrane potentiometer).

The information received from the sensor is processed in order to determine whether the ergonomic characteristic of the user is within a reference ergonomic boundary, 110. In one embodiment, the processing is executed via a CPU/processing module included on the computing device. In another embodiment, the processing is executed outside the computing device (i.e., backend processing). The reference ergonomic boundary may comprise stored data (stored on or off the computing device) representing established ergonomic boundaries. The reference ergonomic boundary may also comprise ergonomic boundaries specific for the user. For example, the user may have characteristics that prevent him from operating the computing device within the established ergonomic boundary (e.g., a medical condition preventing "ideal" posture).

If the user is within the reference ergonomic boundary, then the process awaits further sensor data, 120. In one embodiment, the user may receive some form of positive feedback (e.g., an indication on the sensor or the display of the computing device that the user is within the reference ergonomic boundary).

If the user is not within the reference ergonomic boundary, processing is executed to determine an adjustment for the user to make so that the ergonomic characteristic of the user is within the reference ergonomic boundary, 130. This adjustment may comprise an adjustment to the physical ergonomics of the user, an adjustment to the device, or both. The above processing may be executed via the computing device, or via backend processing.

The user is then notified that ergonomic adjustments are required to bring the user within the reference ergonomic boundary, 140. In one embodiment, the user is notified via the display coupled to the computing device (e.g., an icon on the taskbar of the display, a pop-up window). In another embodiment, the user is notified via a sensor coupled to the user that an ergonomic adjustment is required (e.g., an audio or tactile feedback from the sensor to notify the user that he is not within the reference ergonomic boundary).

Figure 2:
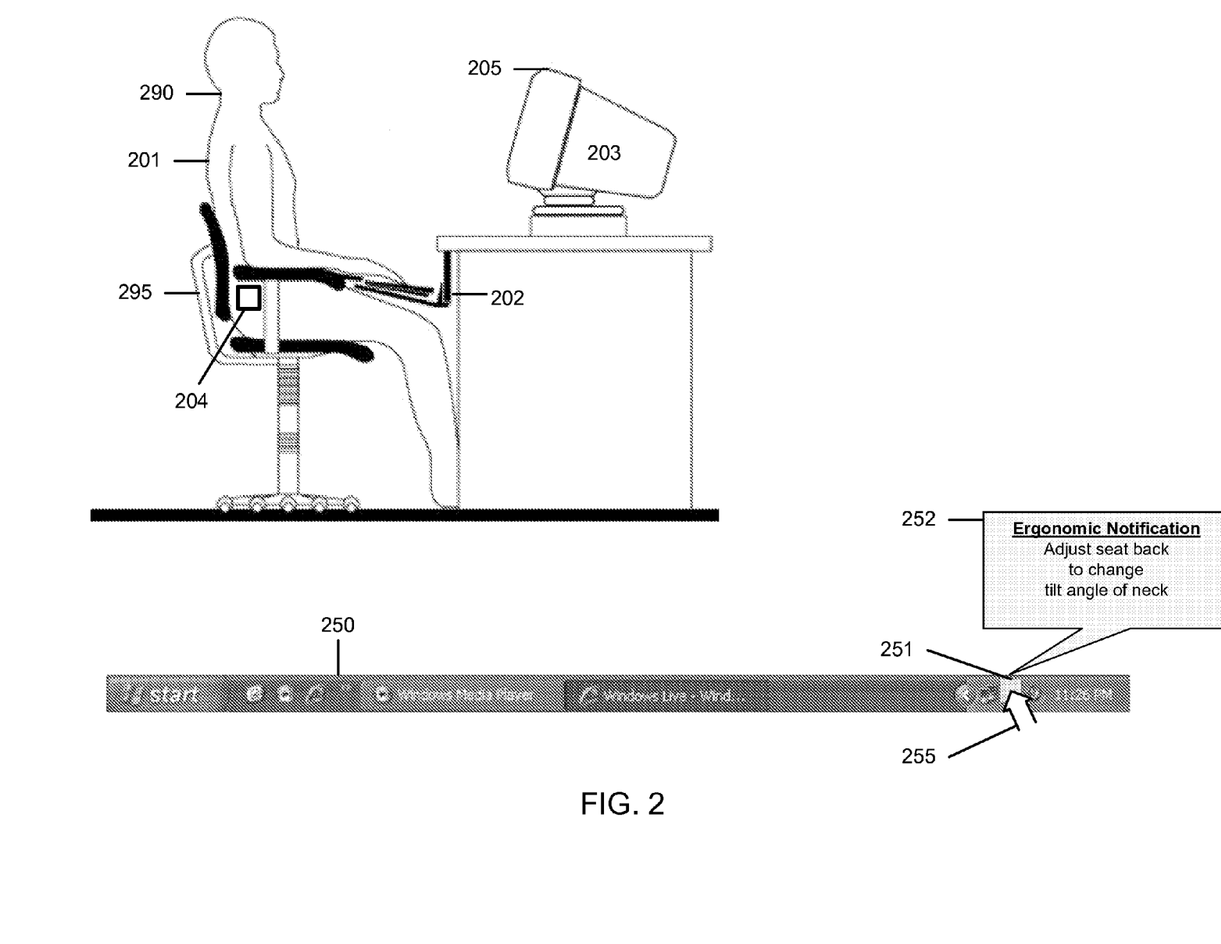
FIG. 2 is a diagram of a computing device user utilizing a sensor to monitor his ergonomic characteristics.

FIG. 2 is a diagram of a computing device user utilizing a sensor to monitor his ergonomic characteristics. In this example embodiment, user 201 is using desktop computer 203. User 201 interacts with computer 203 via keyboard device 202 and display 205. In this embodiment, sensor 204 is an accelerometer coupled to the user's hip to measure the tilt of the user. Data from sensor 204 is wirelessly transmitted to computing device 203 for processing.

In this embodiment, data from sensor 204 is processed to determine whether the user's ergonomic posture, specifically the tilt angle of the user's back 290, is within a reference ergonomic boundary stored on desktop computer 203. For example, the reference ergonomic boundary may indicate that the tilt angle of the user's back 290 should be tilted between 85 and 95 degrees with respect to the x-axis. In this diagram, the tilt angle of the user's back is not within said reference boundary. Processing may further determine an adjustment, or a plurality of adjustments, for the user to make in order for his ergonomic posture to be within the reference ergonomic boundary.

The user is notified of the required ergonomic adjustments via display 205—as illustrated by taskbar icon 251 included in taskbar 250. In this embodiment, sensor 204 may indicate the tilt angle of the user's back is outside the reference ergonomic boundary via an audio (e.g., a beep) or a physical (e.g., vibration) indicator. The user may then hover cursor 255 over taskbar icon 251 to reveal information balloon 252. In this embodiment, processing determines that seat back 295 should be adjusted to bring the user's back posture within the reference ergonomic boundary.

In addition to the sensor indicating the need for ergonomic adjustments, taskbar icon 251 may indicate when a user's ergonomic posture is within the reference ergonomic boundary (e.g., the icon may be displayed in green when the user is within the reference ergonomic boundary and red when the user is outside the boundary).

Figure 3:
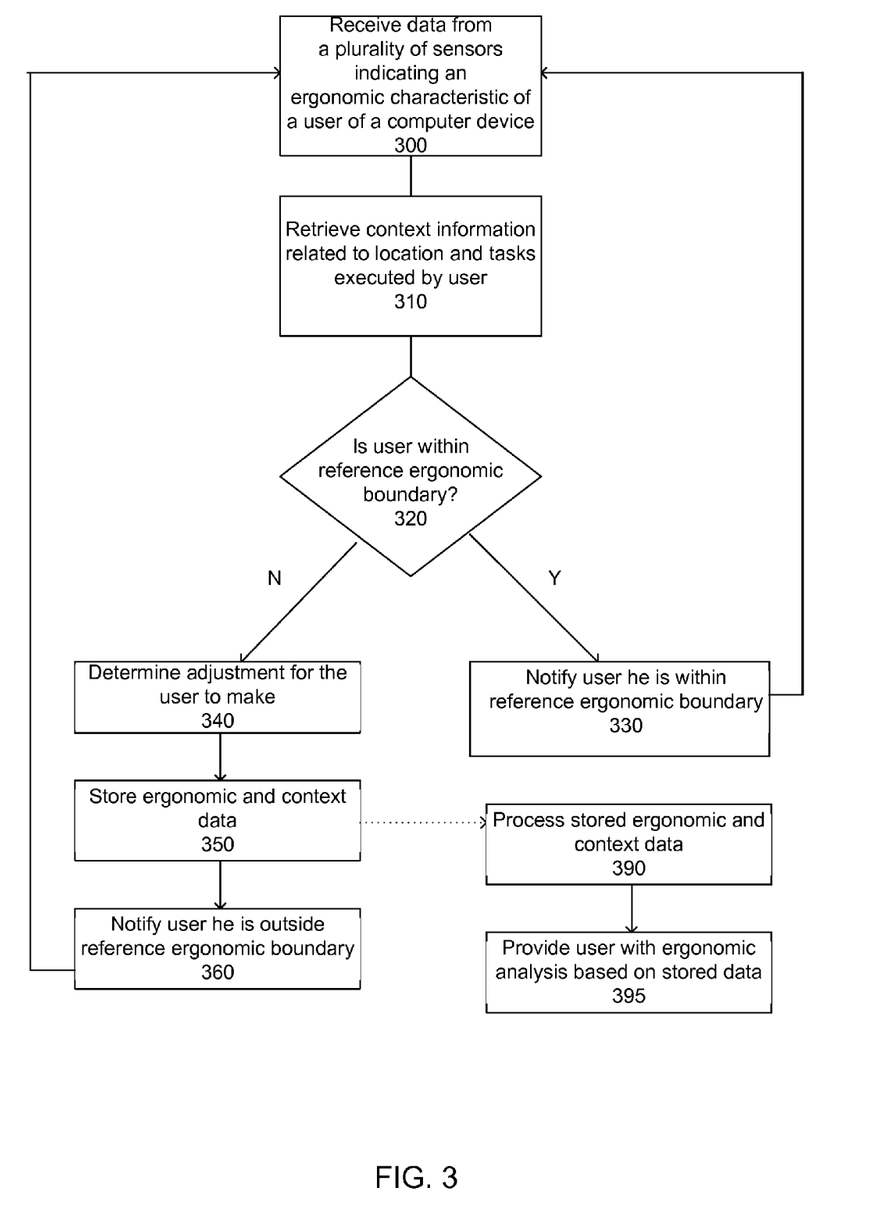
FIG. 3 is a flow diagram of an embodiment of a process for ergonomic data capture and processing using information capture via a plurality of sensors and context data relating to the location and use of a computing device.

FIG. 3 is a flow diagram of an embodiment of a process for ergonomic data capture and processing using information captured via a plurality of sensors and context data relating to the location and use of a computing device.

Data is received from a plurality of sensors, including at least one sensor coupled to the user and at least one sensor coupled to the device, 300. The plurality of sensors may include or be a combination of any of the following: an orientation sensor coupled to the user's body (e.g., the user's hip) for posture sensing; an orientation sensor coupled to the display of the computing device for screen tilt or device orientation sensing; an image sensor (e.g., a camera) placed in a position to view the eyes of the user to determine the user's eye-blink rate or the display orientation; a microphone positioned near a keyboard of the computing device to audibly capture the volume of the user's key strokes; a pressure sensor under the keys of the keyboard of the computing device; an external light sensor; a distance sensor (e.g., an infrared sensor) coupled to either the user or the display; and a position/pressure sensor (e.g., a membrane potentiometer) placed in front of the keyboard of the computing device.

In addition to the sensor data, context information relating to the location and tasks executed by the user may be retrieved 310. A clock may be included on the computing device or one of the sensors to indicate the time of use. A location sensor or device (e.g., a device using GPS, GSM or WiFi triangulation techniques) may be included on the user or the device to determine the location of the user. Context information relating to the time of data and current use of the computer (e.g., historical logged data pertaining to computing device use, MS Outlook schedule information, etc.) may also be retrieved from the computing device (e.g., from non-volatile storage of the computing device).

Sensor data and context information may be used to determine whether the user's ergonomics are within a reference ergonomic boundary, 320. Context information may also be used to determine whether it is appropriate to interrupt the user at a given time. Data from the orientation sensor coupled to the user's hip may be used to determine whether an adjustment to the tilt of the user's body and extremities is required. Data from the orientation sensor coupled to the display of the computing device may be used to determine whether an adjustment the tilt of the display with respect to the user is required. Data from the camera placed with respect to the eyes of the user may be used to determine whether an adjustment is required for the blink-rate of the user as the user looks at the display of the computing device, or whether an adjustment to the height of the display with respect to the user's eyes is required (e.g., positioning the monitor so that the top edge of the monitor is at eye level). Data from the microphone or data from the pressure sensor under the keys of the keyboard may be used to determine whether an adjustment to the pressure exerted by the user on the keys of the keyboard during typing is required. Data from the external light sensor may be used to determine whether an adjustment to the ambient light level is required. Data from the infrared sensor coupled to either the user or the display of the computing device may be used to determine whether an adjustment to the distance between the user and the display is required. Data from the position/pressure sensor (e.g., a membrane potentiometer) may be used to determine whether an adjustment to the wrist placement of the user with respect to the keyboard is required.

Data from the plurality of sensors may also be processed in combination to determine an ergonomic characteristic of the user. For example, the elbow carrying angle of a laptop user may be determined by a function of data from a camera (indicating the vertical height of the laptop with respect to the user's face), data from an IR sensor (indicating the distance between the user and the laptop), and data from a tilt sensor coupled to the display of the laptop (indicating the angle of the display of the laptop with respect to the user's lap).

If the user's ergonomics are within the reference ergonomic boundary, then an indicator is displayed to the user, 330, and the process waits for further information from the plurality of sensors.

If the user's ergonomics are not within the reference boundary, then the sensor data, in conjunction with the context data, is processed to further determine the adjustment (or adjustments) necessary to bring the user within the reference ergonomic boundary, 340. Context information may indicate, for example, that the user is at his workplace, and thus the processing may take into account what may and may not be adjusted (e.g., non-adjustable display, limited work space). Context information may further include user history that limits the possible ergonomic adjustments (e.g., a medical condition to prevent certain postures, handedness). Context information may further include the activities the user is engaged in, thus explaining a non-ideal ergonomic posture (e.g., transcribing a document, thus requiring the user's posture to enable him to view both the document and the display of the computing device).

Data indicating the user was outside the ergonomic boundary and the context data indicating where the user was and what the user was doing may be stored in non-volatile storage to indicate ergonomic trends of the user, 350. Ergonomic trends of the user may be analyzed for long-term ergonomic advice. For example, stored ergonomic and context data may be transmitted for backend processing, 390. Backend processing may determine long-term solutions for the user to make to reduce or eliminate "poor" ergonomics of the user, 395. For example, stored ergonomic and context data may indicate that the user is frequently alerted to change his back posture with relation to the display of the computing device while the user is at work. Backend processing may determine that the user should, for example, change his office chair or change the display of the computer, or recommend ergonomic exercises for the user to execute. Backend processing may further determine the likelihood or severity of an RSI injury.

An indicator is displayed to notify the user that he is currently outside the reference ergonomic boundary, 360. The process will then await further information from the plurality of sensors.

Figure 4A:
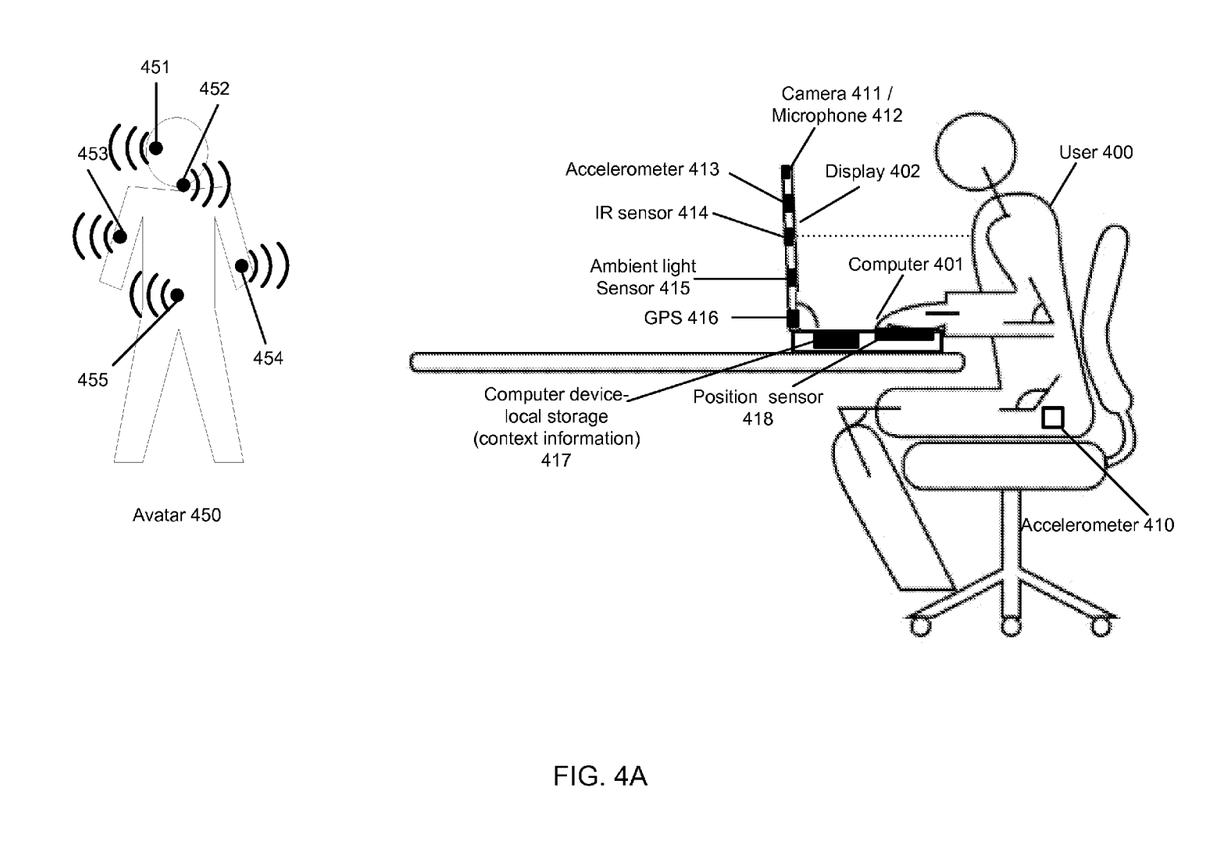
FIG. 4A illustrates a user utilizing a computing device with a plurality of sensors.

FIG. 4A illustrates a user 400 utilizing a computing device 401 with the following sensors: accelerometer 410 coupled to the hip of user 400; camera 411 to detect user's eye-blink rate and/or height of the monitor 402 with respect to the user's eyes; microphone 412 to detect sound/volume of key strokes; accelerometer 413 to determine tilt of monitor 402; IR sensor 414 to determine the distance between monitor 402 and user 400; ambient light sensor 415; and placement sensor 418 to detect wrist placement of user 400.

In addition to the above sensor data, context information may be used in the analysis of the ergonomics of user 400. GPS sensor 416 (to provide location information) and device local storage 417 (to provide task information, e.g., MS Outlook schedule information) may be used to provide the context information.

FIG. 4A also illustrates an avatar 450 highlighting the ergonomic problem areas of the user. Avatar 450 may be displayed on the display of computing device 401 in any manner (e.g., pop-up window, taskbar icon). In this figure, avatar 450 includes a plurality of indicators to notify the user of ergonomic issues determined by processing data from the sensors and context data: eye problem indicator 451, neck problem indicator 452, elbow problem indicator 453, wrist problem indicator 454 and spinal problem indicator 455.

In one embodiment, hovering a cursor one of the indicators of the avatar will notify the user of suggested ergonomic adjustments to make in order to bring the user within the reference ergonomic boundaries. For example, eye problem indicator 451 may recommend adjusting the tilt of monitor 402; neck problem indicator 452 may recommend adjusting the tilt of the head of user 400; elbow problem indicator 453 may recommend adjusting the elbow carrying angle of user 400; wrist problem indicator 454 may recommend user 400 adjust the pressure of his keystrokes and lift his wrists from the keyboard of computing device 401; and spinal problem indicator 455 may recommend user 400 adjust the angle of his lower lumbar and angle of his knees.

Figure 4B:
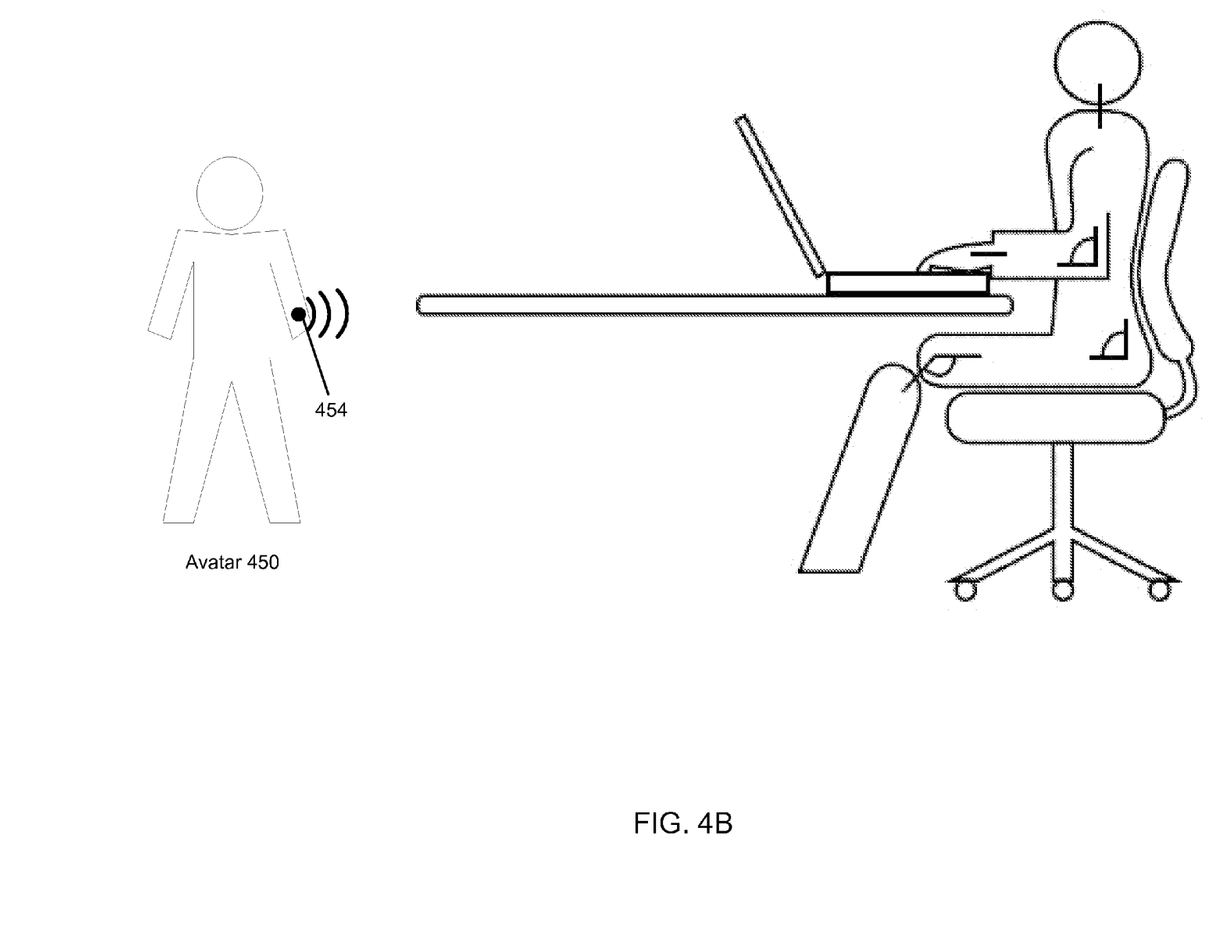
FIG. 4B illustrates a user making adjustments suggested by a user interface.

FIG. 4B illustrates user 400 making adjustments suggested by the user interface, specifically, adjusting the tilt of the monitor, adjusting the tilt of his head, adjusting the his elbow carrying angle, adjusting the pressure of his keystrokes (not illustrated), adjusting the angle of his lower lumbar and the angle of his knees. User 400 has not corrected his/her wrist placement with respect to the keyboard, so avatar 450 still indicates the user's wrists as an ergonomic problem area via wrist problem indicator 454. In this example, wrist problem indicator 454 may recommend user 400 lift his wrist from the keyboard of computing device 401.

Various components referred to above as processes, servers, or tools described herein may be a means for performing the functions described. Each component described herein includes software or hardware, or a combination of these. The components can be implemented as software modules, hardware modules, special-purpose hardware (e.g., application specific hardware, ASICs, DSPs, etc.), embedded controllers, hardwired circuitry, etc. Software content (e.g., data, instructions, configuration) may be provided via an article of manufacture including a computer storage readable medium, which provides content that represents instructions that can be executed. The content may result in a computer performing various functions/operations described herein. A computer readable storage medium includes any mechanism that provides (i.e., stores and/or transmits) information in a form accessible by a computer (e.g., computing device, electronic system, etc.), such as recordable/non-recordable media (e.g., read only memory (ROM), random access memory (RAM), magnetic disk storage media, optical storage media, flash memory devices, etc.). The content may be directly executable ("object" or "executable" form), source code, or difference code ("delta" or "patch" code). A computer readable storage medium may also include a storage or database from which content can be downloaded. A computer readable medium may also include a device or product having content stored thereon at a time of sale or delivery. Thus, delivering a device with stored content, or offering content for download over a communication medium may be understood as providing an article of manufacture with such content described herein.

The invention claimed is:

1. A method comprising:
receiving information, via at least one sensor included in a sensor device coupled to a user, indicating an ergonomic characteristic of the user of a computing device in relation to a use of the computing device, wherein the at least one sensor of the sensor device comprises at least one of an accelerometer or a gyroscope to detect user movement;
determining, based on the received information, if the ergonomic characteristic of the user is within a reference ergonomic boundary; and
in response to determining the ergonomic characteristic of the user is not within the reference ergonomic boundary:
determining an adjustment for the user to make so that the ergonomic characteristic of the user, in relation to the use of the computing device, is within the reference ergonomic boundary, by:
determining a context of the user utilizing the computing device;
determining an adjustment to the ergonomic characteristic of the user based on the context of the user; and
determining an adjustment to the computing device based on the context of the user, and
notifying the user, via tactile feedback from the sensor device coupled to the user, that the ergonomic characteristic is not within the reference ergonomic boundary
determining, via an orientation sensor coupled to a display of the computing device and separate from the sensor device coupled to the user, a spinal position of the user, wherein the adjustment includes at least one of:
adjusting a seating position of the user with respect to the computing device, or
adjusting a position of the display of the computing device with respect to the user.

2. The method of claim 1, wherein notifying the user includes displaying the adjustment via a user interface, the user interface to be displayed on the computing device.

3. The method of claim 1, wherein determining an adjustment to the ergonomic characteristic of the user based on the context of the user comprises determining an adjustment to the ergonomic characteristic and determining an adjustment to the computing device based on the context of the user comprises determining an adjustment based on a location of the computing device.

4. The method of claim 1, further comprising
storing the information indicating the ergonomic characteristic of the user, the stored information to be processed to determine ergonomic trends of the user.

5. The method of claim 1, further comprising:
determining, via an image sensor separate from the sensor device, an eye-blink rate of the user, wherein the adjustment includes adjusting the eye-blink rate of the user.

6. The method of claim 1, wherein the at least one sensor included in the sensor device coupled to the user includes an orientation sensor, the ergonomic characteristic of the user includes the spinal position of the user, and the adjustment includes adjusting a seating position of the user with respect to the computing device.

7. The method of claim 1, further comprising:
determining, via a distance sensor coupled to the computing device, a distance between the user and the computing device, wherein the adjustment includes changing the distance between the user and the computing device.

8. A system comprising:
a computing device;
a sensor device coupled to a user of a computing device and including at least one sensor to capture data indicating an ergonomic characteristic of the user of the computing device in relation to a use of the computing device, wherein the at least one sensor of the sensor device comprises at least one of an accelerometer or a gyroscope to detect user movement;
non-volatile storage to receive and store the captured data indicating the ergonomic characteristic of the user;
a processor to execute the captured data the non-volatile storage to:
determine, based on the captured data, if the ergonomic characteristic of the user is within a reference ergonomic boundary, and
in response to determining the ergonomic characteristic of the user is not within the reference ergonomic boundary, determine an adjustment for the user to make so that the ergonomic characteristic of the user, in relation to the use of the computing device, is within the reference ergonomic boundary, by determining a context of the user utilizing the computing device, determining an adjustment to the ergonomic characteristic of the user based on the context of the user; and determining an adjustment to the computing device based on the context of the user;
transmit data to the sensor device to notify the user, via tactile feedback from the sensor device coupled to the user, that the ergonomic characteristic is not within the reference ergonomic boundary;
determine, via an orientation sensor coupled to a display of the computing device and separate from the sensor device coupled to the user, a spinal position of the user, wherein the adjustment includes at least one of:
adjust a seating position of the user with respect to the computing device, or
adjust a position of the display of the computing device with respect to the user.

9. The system of claim 8, wherein the notification module is to further transmit display data to the computing device to display the adjustment via a user interface, the user interface to be displayed via the computing device.

10. The system of claim 8, wherein determining an adjustment to the ergonomic characteristic of the user based on the context of the user comprises determining an adjustment to the ergonomic characteristic and determining an adjustment to the computing device based on the context of the user comprises determining an adjustment based on a location of the computing device.

11. The system of claim 8, wherein the non-volatile storage is to further store ergonomic trends of the user, and wherein the reference ergonomic boundary is based, at least in part, on the stored ergonomic trends of the user.

12. The system of claim 8, further comprising:
a position and placement sensor coupled to the computing device to determine the user's wrist placement with respect to a keyboard of the computing device, the ergonomic characteristic of the user includes whether the user's wrists are resting on the keyboard and the pressure exerted on the keyboard by the user's wrists, and the adjustment includes adjusting the wrist position of the user.

13. The system of claim 8, further comprising:
an image sensor, wherein the ergonomic characteristic of the user includes the position of the user's eyes with respect to a display of the computing device, and the adjustment includes at least one of adjusting the eye level of the user with respect to the display of the computing device, or adjusting the height of the display of the computing device with respect to the eye level of the user.

14. The system of claim 8, further comprising
a light sensor to data indicating an ambient light level of the user and the computing device, and the processing module to further:
determine whether the ambient light level is within a reference ergonomic boundary, and
in response to determining the ambient light level is not within the reference ergonomic boundary, determining an adjustment so that the ambient light level is within the reference ergonomic boundary.

15. An article of manufacture comprising a computer-readable storage medium having instructions stored thereon to cause a processor to perform operations including:
receiving information, via at least one sensor included in a sensor device coupled to a user, indicating an ergonomic characteristic of the user of a computing device in relation to a use of the computing device, wherein the at least one sensor of the sensor device comprises at least one of an accelerometer or a gyroscope to detect user movement;
determining, based on the received information, if the ergonomic characteristic of the user is within a reference ergonomic boundary; and
in response to determining the ergonomic characteristic of the user is not within the reference ergonomic boundary:
determining an adjustment for the user to make so that the ergonomic characteristic of the user, in relation to the use of the computing device, is within the reference ergonomic boundary, by:
determining a context of the user utilizing the computing device;
determining an adjustment to the ergonomic characteristic of the user based on the context of the user; and
determining an adjustment to the computing device based on the context of the user, and
notifying the user, via tactile feedback from the sensor device coupled to the user, that the ergonomic characteristic is not within the reference ergonomic boundary
determining, via an orientation sensor coupled to a display of the computing device and separate from the sensor device coupled to the user, a spinal position of the user, wherein the adjustment includes at least one of:
adjusting a seating position of the user with respect to the computing device, or
adjusting a position of the display of the computing device with respect to the user.

16. The article of manufacture of claim 15, wherein notifying the user includes displaying the adjustment via a user interface, the user interface to be displayed on the computing device.

17. The article of manufacture of claim 15, wherein determining an adjustment to the ergonomic characteristic of the user based on the context of the user comprises determining an adjustment to the ergonomic characteristic based on a physical limitation of the user and determining an adjustment to the computing device based on the context of the user comprises determining an adjustment based on a location of the computing device.

18. The article of manufacture of claim 15, further comprising
storing the information indicating the ergonomic characteristic of the user, the stored information to be processed to determine ergonomic trends of the user.

\* \* \* \* \*